United States Patent
Lee et al.

(10) Patent No.: US 12,036,562 B2
(45) Date of Patent: Jul. 16, 2024

(54) ION GENERATING DEVICE, METHOD FOR MANUFACTURING SAME, AND AIR CONDITIONER

(71) Applicant: LG ELECTRONICS INC., Seoul (KR)

(72) Inventors: Sanggu Lee, Seoul (KR); Bongjo Sung, Seoul (KR); Kyungsoo Yoon, Seoul (KR); Jihyun Kim, Seoul (KR)

(73) Assignee: LG ELECTRONICS INC., Seoul (KR)

(*) Notice: Subject to any disclaimer, the term of this patent is extended or adjusted under 35 U.S.C. 154(b) by 610 days.

(21) Appl. No.: 17/207,997

(22) Filed: Mar. 22, 2021

(65) Prior Publication Data

US 2021/0205821 A1 Jul. 8, 2021

Related U.S. Application Data

(62) Division of application No. 16/061,897, filed as application No. PCT/KR2016/013375 on Nov. 18, 2016, now abandoned.

(30) Foreign Application Priority Data

Dec. 14, 2015 (KR) .................. 10-2015-0178435

(51) Int. Cl.
*G03F 7/20* (2006.01)
*A61L 9/22* (2006.01)
*B01D 53/32* (2006.01)
*B03C 3/32* (2006.01)
*B03C 3/68* (2006.01)
*B03C 3/82* (2006.01)
*B81C 1/00* (2006.01)
*C01B 13/11* (2006.01)
*F24F 1/0076* (2019.01)
*G03F 7/30* (2006.01)
*H01L 21/02* (2006.01)
*B03C 3/00* (2006.01)
*B03C 3/38* (2006.01)
*F24F 8/30* (2021.01)

(52) U.S. Cl.
CPC .................. *B03C 3/32* (2013.01); *A61L 9/22* (2013.01); *B01D 53/32* (2013.01); *B03C 3/68* (2013.01); *B03C 3/82* (2013.01); *B81C 1/00103* (2013.01); *C01B 13/115* (2013.01); *F24F 1/0076* (2019.02); *G03F 7/2014* (2013.01); *G03F 7/30* (2013.01); *H01L 21/02* (2013.01); *A61L 2209/16* (2013.01); *B01D 2257/90* (2013.01); *B01D 2258/06* (2013.01); *B01D 2259/818* (2013.01); *B03C 3/00* (2013.01); *B03C 3/38* (2013.01); *B81C 2201/0101* (2013.01); *F24F 8/30* (2021.01)

(58) Field of Classification Search
CPC .......... G03F 7/2014; G03F 7/213; G03F 7/30; H01L 21/31; H01L 21/3205
See application file for complete search history.

(56) References Cited

U.S. PATENT DOCUMENTS

| | | | |
|---|---|---|---|
| 3,963,489 A * | 6/1976 | Cho | ........................ H01L 21/31 216/36 |
| 6,330,146 B1 | 12/2001 | Blitshteyn et al. | |
| 7,175,495 B2 | 2/2007 | Nakamoto et al. | |
| 2004/0219706 A1 * | 11/2004 | Wan | ..................... B81C 1/00095 438/455 |
| 2009/0211459 A1 | 8/2009 | Hu et al. | |
| 2015/0228416 A1 * | 8/2015 | Hurwitz | ............... H01G 4/1209 174/257 |
| 2016/0320332 A1 | 11/2016 | Hsiung et al. | |
| 2016/0369412 A1 | 12/2016 | Krasovic | |

FOREIGN PATENT DOCUMENTS

| | | |
|---|---|---|
| JP | 2006-029691 | 2/2006 |
| JP | 2006-049227 | 2/2006 |
| KR | 10-2004-0092576 | 11/2004 |
| KR | 10-2005-0098567 | 10/2005 |
| KR | 10-2008-0012120 | 2/2008 |
| KR | 10-0906465 | 7/2009 |
| KR | 10-2010-0101792 | 9/2010 |
| KR | 10-2011-0041021 | 4/2011 |
| KR | 10-2011-0079123 | 7/2011 |

OTHER PUBLICATIONS

International Search Report (with English Translation) and Written Opinion dated Mar. 10, 2017 issued in Application No. PCT/KR2016/013375.
Korean Notice of Allowance dated May 23, 2017.
Korean Office Action dated Jul. 27, 2017.
United States Office Action dated Aug. 13, 2020 issued in co-pending related U.S. Appl. No. 16/061,897.
United States Office Action dated Jan. 22, 2021 issued in co-pending related U.S. Appl. No. 16/061,897.

* cited by examiner

Primary Examiner — Daborah Chacko-Davis

(74) Attorney, Agent, or Firm — KED & ASSOCIATES (57) ABSTRACT

An ion generating device, a method for manufacturing an ion generating device, and an air conditioner are provided. The ion generating device may include a discharge electrode that generates ions, and a power supply that applies power to the discharge electrode. The discharge electrode may include a support formed of a conductor, and a discharge pin formed to protrude from a surface of the support and having a tip. The discharge pin may include nickel (Ni).

13 Claims, 7 Drawing Sheets

ION GENERATING DEVICE, METHOD FOR MANUFACTURING SAME, AND AIR CONDITIONER

CROSS-REFERENCE TO RELATED APPLICATIONS

This application is a Divisional of prior U.S. patent application Ser. No. 16/061,897 filed Jun. 13, 2018, which is a National Stage application of International Patent Application No. PCT/KR2016/013375 filed on Nov. 18, 2016, which claims priority to Korean Application No. 10-2015-0178435 filed in Korea on Dec. 14, 2015, whose entire disclosures are hereby incorporated by reference.

BACKGROUND

1. Field

An ion generating device, a method for manufacturing the same, and an air conditioner are disclosed herein.

2. Background

Recently, buildings are designed to minimally introduce external air and are hermetically constructed to save energy, so contamination of the indoor air becomes worse. Accordingly, various rules about indoor contaminants are increasingly enhanced.

Operating appliances in houses or offices produce indoor contaminants. These contaminants either accumulate in the appliance or discharge out of the appliance. These indoor contaminants may stink and may have adversely affect sanitation.

For example, the inside and the outside of appliances that use air containing moisture or water, such as an air conditioner, a dehumidifier, an air cleaner, a refrigerator, or a washing machine, may be contaminated by dust or microorganisms.

An ion generating device that generates negative ions may be used to make contaminated indoor air clean and there is a technology related to an ion generating device as follows in the related art.

Korean Patent Application Publication No.: 10-2005-0098567, Title: Ion generator using carbon nano tip and manufacturing method thereof, Publication date: Oct. 12, 2005.

Meanwhile, according to the ion generator of the related art, it is required to increase voltage in order to generate high-density negative ions, and in this process, ozone and noise are increased. Further, according to the ion generator of the related art, distribution of negative ions generated at a discharge electrode is reduced by a grounding electrode.

An object of the present invention is to provide an ion generating device having a minimized discharge pin to generate high-density ions even without increasing voltage that is applied.

Another object of the present invention is to effectively distribute ions generated at a discharge electrode.

Another object of the present invention is to reduce noise generated when an ion generating device is operated.

In order to generate high-density ions, a discharge pin having a tip and disposed at a discharge electrode is manufactured by a MEMS process.

When the discharge pin is manufactured by the MEMS process, a silicon substrate having a crystal direction (100) is wet-etched by potassium hydroxide (KOH) and then the etched portion is plated with metal, thereby forming the discharge pin. The discharge pin may be made of nickel.

A Platinum (Pt) coating may be formed on the discharge pin to improve discharge efficiency.

In order to effectively distribute generated ions, ions are generated only by a discharge electrode and a power supply without a grounding electrode.

In order to reduce discharge noise, DC voltage can be applied to the discharge electrode from a power supply.

According to an embodiment, it is possible to manufacture having a minimized size using a MEMS process. Further, since a discharge pin having a minimized radius at the tip is used, ions can be generated at relatively low voltage.

Further, there is no grounding electrode, so ions generated by the discharge electrode can be effectively distributed.

It is possible to reduce discharge noise, as compared with using pulse voltage, by applying DC voltage to the discharge electrode.

BRIEF DESCRIPTION OF THE DRAWINGS

Embodiments will be described in detail with reference to the following drawings in which like reference numerals refer to like elements, and wherein.

DETAILED DESCRIPTION

Hereinafter, detailed embodiments will be described with reference to the drawings. However, the spirit is not limited to the proposed embodiments and other embodiments may be easily proposed by those skilled in the art without departing from the scope.

Figure 1:
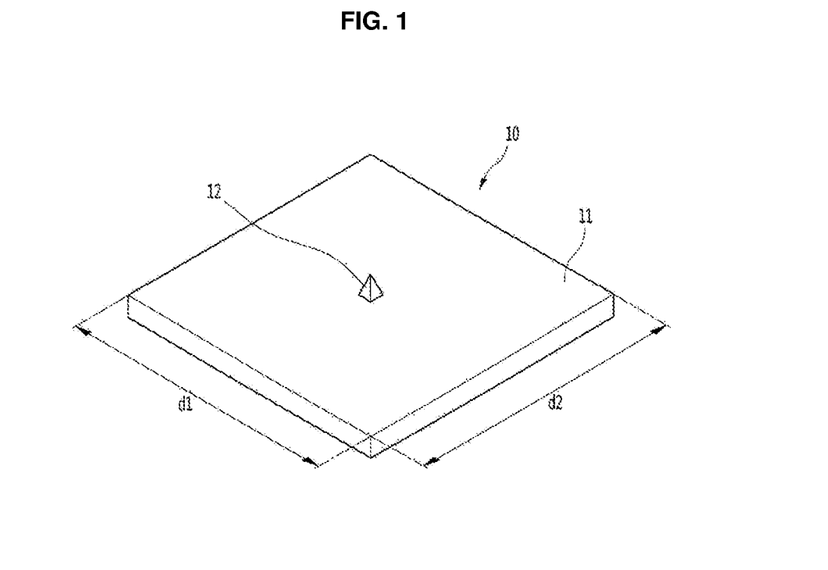
FIG. 1 is a perspective view of an ion generating device according to an embodiment.
Figure 2:
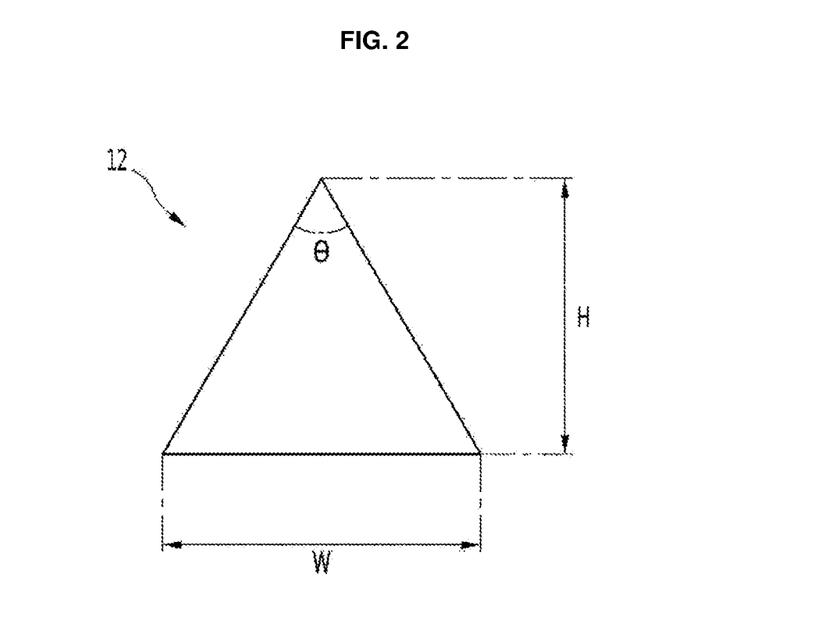
FIG. 2 is a side view of the discharge pin shown in FIG. 1.

FIG. 1 is a perspective view of an ion generating device according to an embodiment and FIG. 2 is a side view of the discharge pin shown in FIG. 1.

Referring to FIGS. 1 and 2, an ion generating device 10 according to an embodiment includes a bed or support 11 and a discharge pin 12. The discharge pin 12 may protrude from a top or surface of the bed 11 or may be integrally formed. The bed 11 and the discharge pin 12 may be, in combination, referred to as a discharge electrode.

The bed 11 may be a plate-shaped conductor and voltage applied from the outside can be transmitted to the discharge pin 12 through the bed 11.

A width d1 and length d2 of the bed 11 may be 5 mm, but this is only an example and embodiments are not limited thereto.

The discharge pin 12 may be disposed on the surface of the bed 11. The discharge pin 12 may be formed in a pyramid shape, that is, a square-based pyramid shape with a tip. A width W and height H of the discharge pin 12 may be 10 μm. However, the shape of the discharge pin 12 is not limited to these shapes and will be described in detail with reference to FIG. 19.

The ion generating device 10 may further include a power supply (not shown). The power supply can be connected to the bed 11 and can apply voltage for discharging.

When power is supplied to the bed 11, the air discharge occurs at the discharge pin 12. A high voltage is applied to the tip of the discharge pin 12.

In this case, a large amount of electrons are emitted around the discharge pin 12 and are bonded to oxygen molecules, whereby negative ions can be generated. That is, the ion generating device 10 may be an electron emission type ion generating device.

As described above, the ion generating device 10, unlike ion generators in the related art, can perform air discharge using only the discharge pin 12 without a grounding electrode. Accordingly, the ion generating device 10 can be reduced in size. Further, since there is no grounding electrode, the flow path of the ions generated from the discharge pin 12 is not blocked, so the ions can be easily distributed.

The power supply can apply DC voltage to the discharge electrode. For example, the power supply may include a rectifier for converting AC into DC. As described above, DC voltage is applied to the discharge electrode, noise to puls voltage is reduced.

The more the tip of the discharge pin 12 is pointed, that is, the higher the kurtosis of the discharge pin 12, the more the air discharge can occur even at low voltage. This is because the smaller the radius at the end of the discharge pin 12, the higher the voltage is applied to the end.

Accordingly, the more the end of the discharge pin 12 is pointed, the more the intensity of the voltage applied to the ion generating device 10 can be decreased. As the intensity of voltage applied is reduced, the amount of ozone and discharge noise generated in air discharge by the discharge pin 12 can be reduced.

In order to minimize the radius of the end of the discharge pin 12, the discharge pin 12 is manufactured by micro electro mechanical systems (hereafter, referred to as "MEMS"). MEMS uses a semiconductor nano/micro manufacturing process that repeats deposition and etching and hyperfine mechanical structures manufactured by MEMS have precision under micrometers. A MEMS process has the advantage that hyperfine mechanical structures can be manufactured in large quantities at a low cost.

An angle θ of the discharge pin 12 manufactured by a MEMS process may be 57.4°. The manufacturing method of the discharge pin 12 will be described below in detail with reference to FIG. 4.

As described above, the ion generating device 10 can keep the surrounding air pleasant by generating negative ions. Accordingly, the ion generating device 10 can be installed in an air conditioner etc. An air conditioner according to an embodiment is described hereafter.

Figure 3:
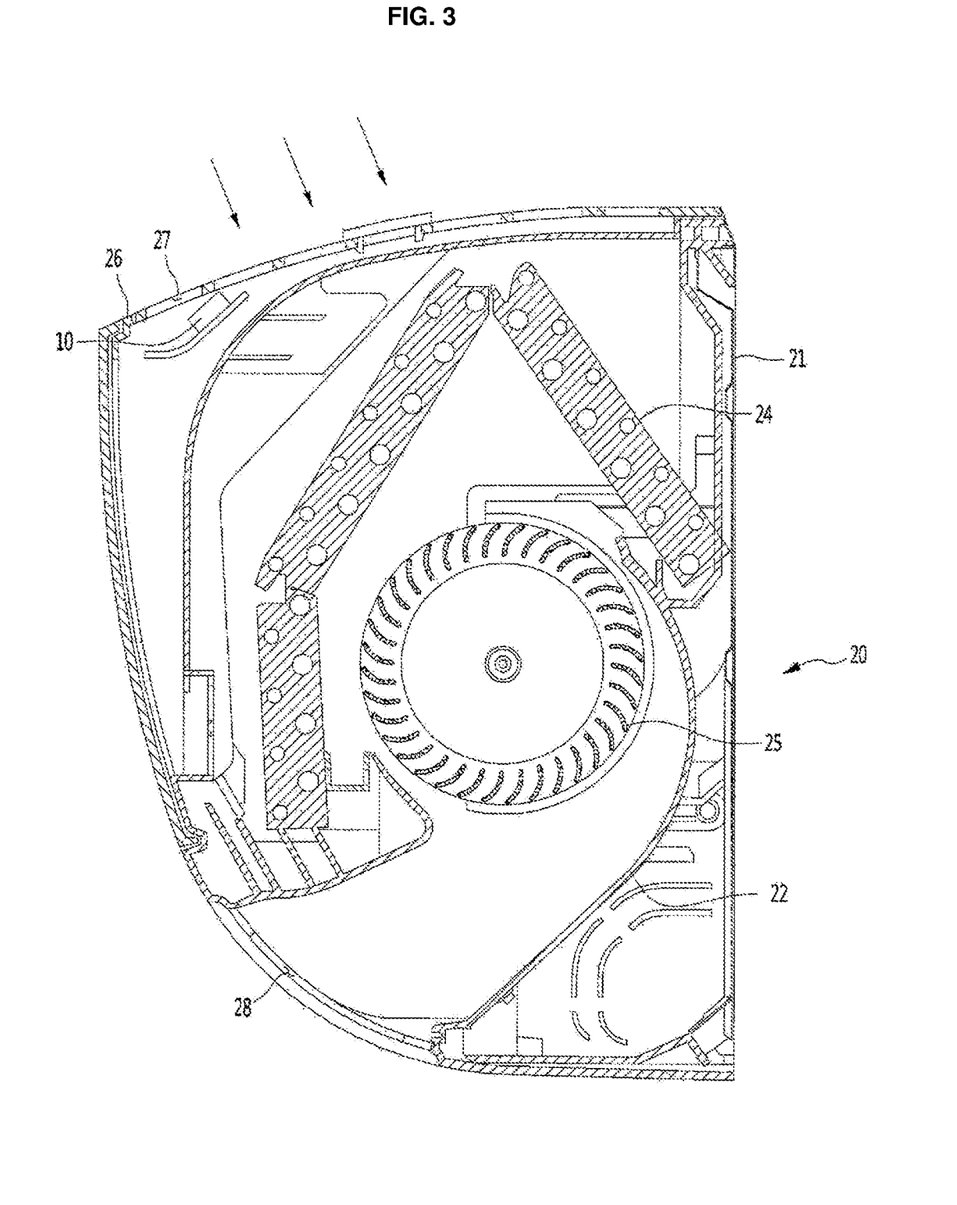
FIG. 3 is a cross-sectional view of an air conditioner equipped with the ion generating device shown in FIG. 1.

FIG. 3 is a cross-sectional view of an air conditioner equipped with the ion generating device shown in FIG. 1.

Referring to FIG. 3, an air conditioner 20 according to an embodiment includes a body 21 accommodating several parts or components and the ion generating device 10 disposed in the body 21 and generating ions.

The body 21 includes a rear frame 22 and a front frame 26 that form an external shape of the body 21. A space for installing various parts or components is defined between the front frame 26 and the rear frame 22.

An indoor heat exchanger 24 in which heat is exchanged between indoor air and a refrigerant and a fan 25 for forcibly blowing the indoor air may be disposed in the internal space of the body 21. The main body 21 has an intake port 27 for suctioning indoor air and an exit or discharge port 28 for discharging the indoor air suctioned in the body 21.

When the fan 25 is operated, the indoor air can be suctioned through the intake port 27, can exchange heat through the indoor heat exchanger 24, and then can be discharged outside through the exit 28.

The ion generating device 10 may be positioned on or in a flow path formed by the fan 242. The ion generating device 10, as shown in the figure, may be disposed close to the intake port 27. Accordingly, ions generated by the ion generating device 10 can be mixed with air blowing by the fan 25.

The air flowing inside through the intake port 27 is mixed with ions while passing by the ion generating device 10 and then flows into the internal space of the body 21, whereby it can sterilize the inside of the body 21.

Alternatively, the ion generating device 10 may be disposed close to the exit 28. In this case, the air that is discharged through the exit 28 is mixed with ions while passing by the ion generating device 10, and is then supplied to the interior. Accordingly, the air that has exchanged heat is mixed with ions immediately before it is supplied to the interior, so floating bacteria and smell in the interior are effectively removed.

The manufacturing method of the ion generating device 10 is described in detail hereafter.

FIGS. 4 to 19 are views sequentially showing a discharge pin that is manufactured by a MEMS technology.

Figure 4:
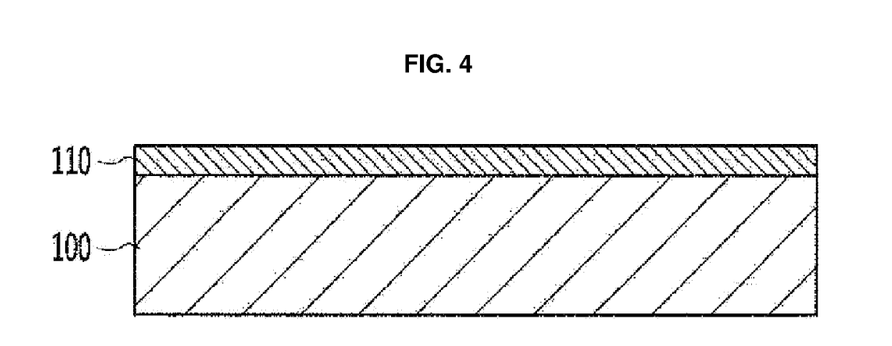
FIGS. 4 to 19 are views sequentially showing a discharge pin that is manufactured by a MEMS technology.
Figure 5:
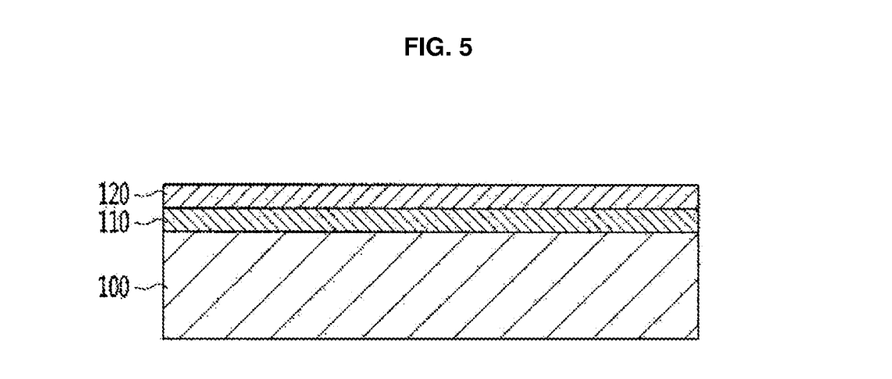

Referring to FIG. 4, a first step is to prepare and clean a substrate 100 and then deposit a sacrifice layer 110 on the substrate 100. The substrate 100 may be made of a silicon wafer having a crystal direction and the sacrifice layer 110 may be made of silicon dioxide.

The sacrifice layer 110 can be deposited on the substrate 100 by low pressure chemical vapor deposition (LPCVD).

Referring to FIG. 2, a second step is to coat a photosensitive resin layer 120 on the sacrifice layer 110. The photosensitive resin includes a photoresist (PR). The photoresist means resin that generates a chemical change when receiving light.

Figure 6:
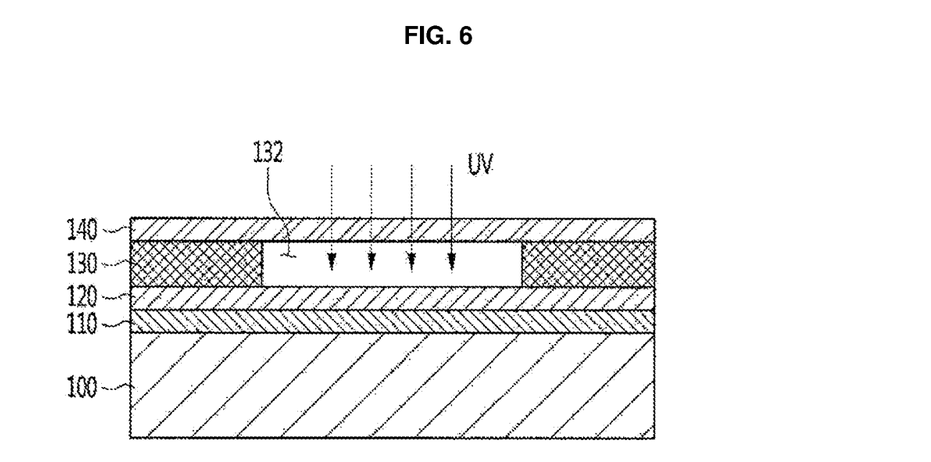

Referring to FIG. 6, a third step is to put a photo mask 130 and 140 on the photosensitive resin layer 120 and form a pattern on the photosensitive resin layer 120 by radiating ultraviolet rays UV.

The photo mask 130 and 140 is formed by plating a chrome (Cr) layer 130 having a predetermined pattern on a glass 140, and ultraviolet rays UV cannot pass through the chrome layer 130. Accordingly, ultraviolet rays UV that are radiated to the photo mask 130 and 140 travel to the photosensitive resin layer 120 through an opening 132 in the chrome layer 130. In the photosensitive resin layer 120, the part not exposed to the ultraviolet rays UV is not changed and the part exposed to the ultraviolet rays is cured.

In the figure, there is only one opening 132 in the chrome layer 130, but a plurality of openings 132 may be provided.

Figure 7:
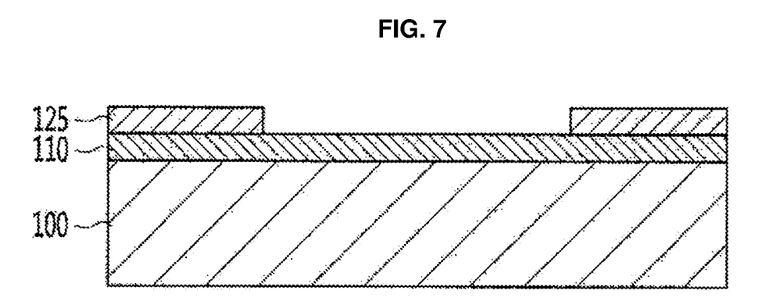

Referring to FIG. 7, a fourth step is to remove the photo mask 130 and 140 and perform development to form a patterned portion 125 from the photo resin layer 120.

The development may be performed by melting the portion, which is cured by ultraviolet rays UV, of the photosensitive resin layer 120, using a solvent. The solvent includes a developing solution.

The photosensitive resin layer 120 is made of positive photosensitive resin. Accordingly, in the photosensitive resin layer 120, the portion overlapping the portion without the pattern of the chrome layer 130 of the photo mask 130 and 140 is removed and only the portion where the pattern of the chrome layer 130 exists remains, so this is called the patterned portion 125.

As described above, since a portion of the photosensitive resin layer 120 is melted, a portion of the top of the sacrifice layer 110 can be exposed to the outside.

Figure 8:
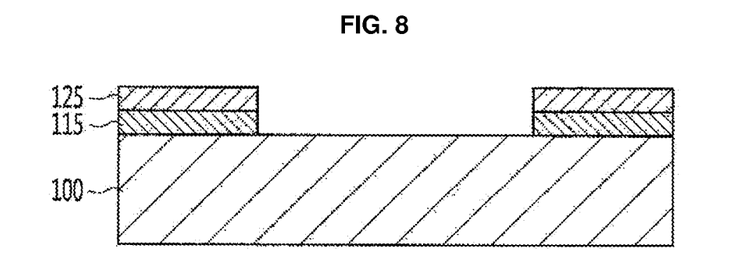

Referring to FIG. 8, a fifth step is to etch the sacrifice layer 110. Etching that is applied to the sacrifice layer 110 may be dry etching. In detail, anisotropic etching that uses fluorine (F)-based gas is applied to the sacrifice layer 110. For example, the gas may include C4F8. Accordingly, in the sacrifice layer 110, only the portion overlapping the patterned portion 125 of the photosensitive resin layer 120 remains. This is called a patterned sacrifice layer 115.

As described above, since a portion of the sacrifice layer 110 is melted, a portion of the top of the substrate 100 can be exposed to the outside.

Figure 9:
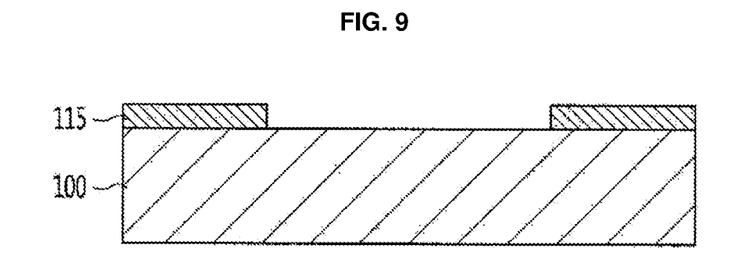

Referring to FIG. 9, a sixth step is to remove the patterned portion 125 of the photosensitive resin layer 120 having the patterned portion 125. The patterned portion 125 of the photosensitive resin layer 120 can be removed by etching and cleansing that uses ethylene. Accordingly, only the substrate 100 and the patterned sacrifice layer 115 on the substrate 100 remain.

Figure 10:
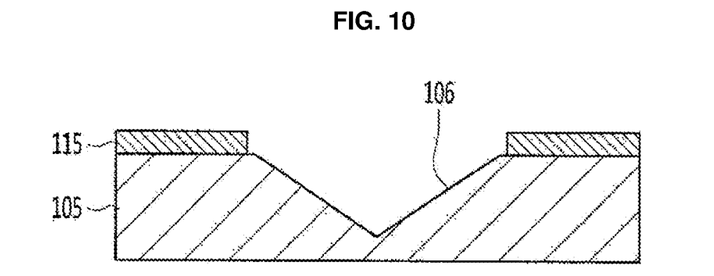

Referring to FIG. 10, a seventh step is to form a substrate 105 with a pattern including an etched shape by etching the substrate 100. In detail, only the portion, which is exposed to the outside and does not overlap the patterned sacrifice layer 115, of the top of the substrate 100 can be etched.

Etching that is applied to the substrate 100 may be wet etching. In detail, anisotropic etching that uses potassium hydroxide (KOH) is applied to the substrate 100. The etched shape by anisotropic etching depends on the crystal direction of silicon and a silicon wafer having a crystal direction is used for the substrate 100, so, as shown in FIG. 10, a shape that is narrowed downward is formed by etching. A plurality of etched shapes 106 may be formed on the substrate 105 with a pattern and the shape of the discharge pin 12 to be manufactured may depend on the etched shapes 106.

The number of the etched shape may depend on the number of the openings 132 of the chrome layer 130. That is, when the chrome layer 130 has a plurality of openings 132, a plurality of etched shapes may be formed on the substrate 105 with a pattern.

Figure 11:
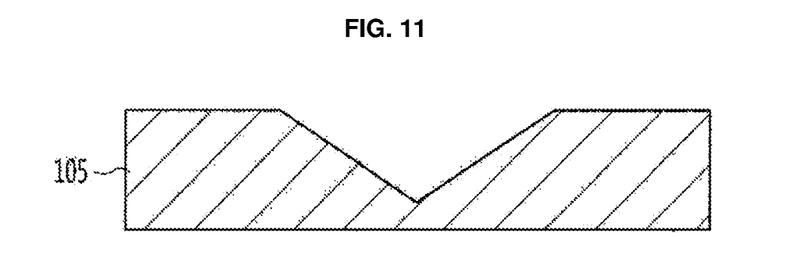

Referring to FIG. 11, an eighth step is to remove and cleanse the patterned sacrifice layer 115. The patterned sacrifice layer 115 can be removed by hydrofluoric acid and cleansing may be performed by sulfuric acid. Accordingly, only the substrate 105 with a pattern remains.

Figure 12:
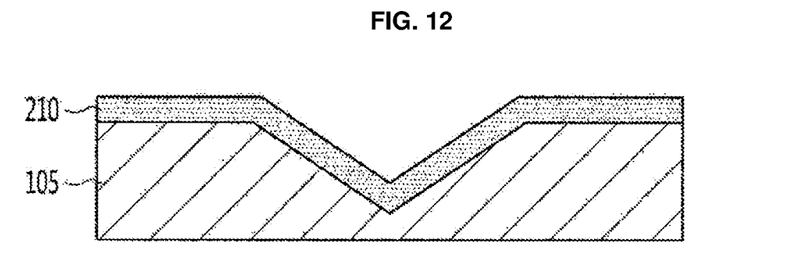

Referring to FIG. 12, a ninth step is to form a seed layer 210 for electroplating on the substrate 105 with a pattern. Metal is deposited in the substrate 105 with a pattern by sputtering. The seed layer 210 may be deposited to corresponding to the pattern shape of the substrate 105. The metal of the seed layer 210 may include copper (Cu).

Figure 13:
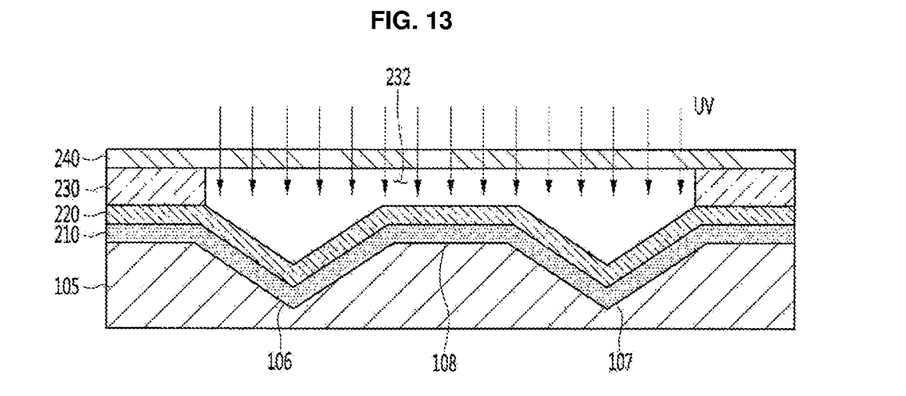

Referring to FIG. 13, a tenth step is to coat a photosensitive resin layer 220 on the seed layer 210, put a photo mask 230 and 240 on the photosensitive resin layer 220, and form a pattern on the photosensitive resin layer 220 by radiating ultraviolet (UV) rays.

The photo mask 230 and 240 includes a glass 240 plated with a chrome layer 230 having a predetermined pattern. Ultraviolet rays UV is radiated to the photosensitive resin layer 220 through an opening 232 of the chrome layer 230. In the photosensitive resin layer 220, the portion exposed to the ultraviolet rays is cured.

A plurality of etched shapes 106 and 107 may be formed on the substrate 105 and the chrome layer 230 may exist outside the etched shapes 106 and 107. Accordingly, ultraviolet rays UV can be radiated to the etched shapes 106 and 107 and the photosensitive resin layer 220 on a ridge 108 between the etched shapes 106 and 107.

Figure 14:
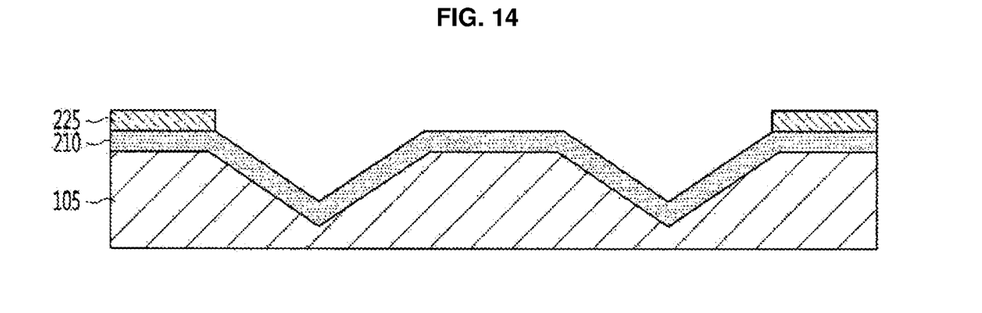

Referring to FIG. 14, an eleventh step is to remove the photo mask 230 and 240 and form a predetermined patterned portion 225 from the photosensitive resin layer 220. The patterned portion 225 is formed by removing a portion of the photosensitive resin layer 220 with ethylene.

The predetermined patterned portion 225 may be formed in a shape surrounding the etched shapes 106 and 107 and the ridge 108 between the etched shapes 106 and 107.

As described above, since a portion of the photosensitive resin layer 220 is removed, a portion of the top of the seed layer 210 can be exposed to the outside.

Figure 15:
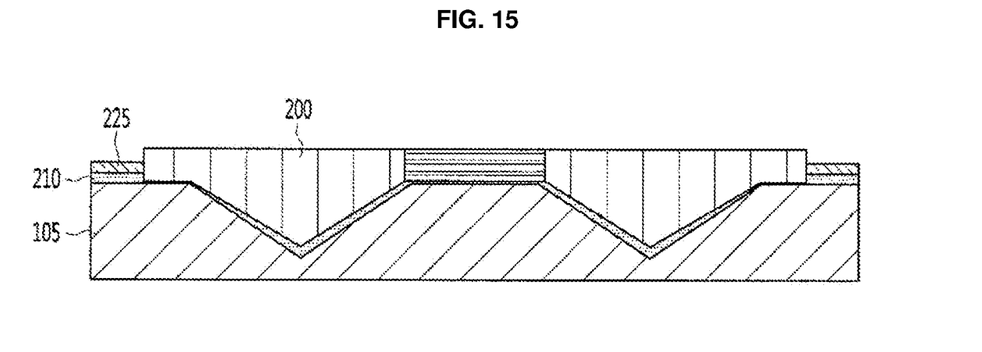

Referring to FIG. 15, a twelfth step is to form a metal layer 200 on the seed layer 210. The metal layer 200 may be formed by electroplating nickel (Ni) on the seed layer 210. The metal layer 200 may be formed higher than the patterned portion 225 of the photosensitive resin layer 220. The metal layer 200 corresponds to the discharge electrode that is formed by a MEMS process. That is, the discharge electrode is formed by plating nickel. Nickel is hard, has high corrosion resistance, and is very lustrous.

Figure 16:
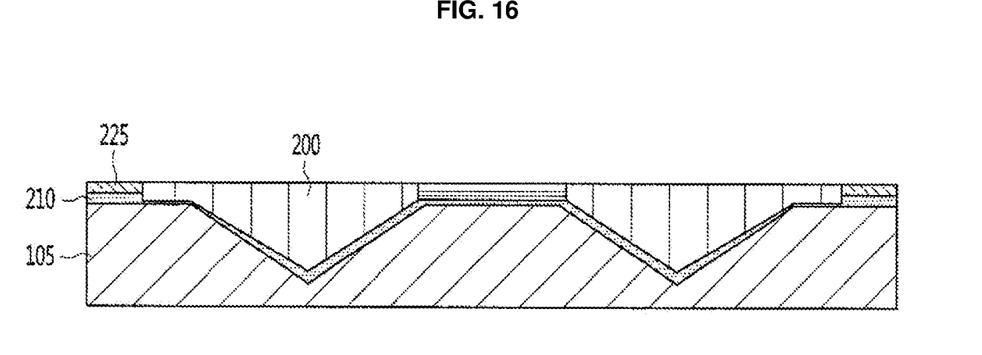

Referring to FIG. 16, a thirteenth step is to planarizing the top of the metal layer 200 through chemical mechanical polishing (CMP).

Figure 17:
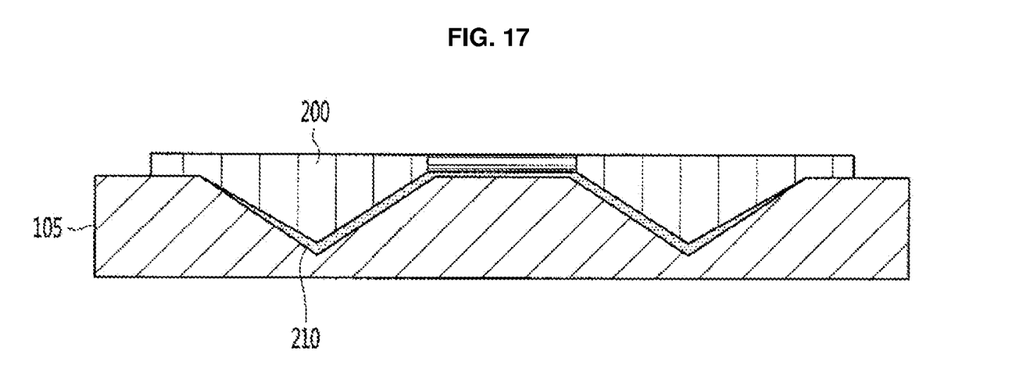

Referring to FIG. 17, a fourteenth step is to partially remove the patterned portion 225 of the photosensitive resin layer 220 and the seed layer 210, using wet etching. The wet etching may be performed by ammonia. Accordingly, only the metal layer 200 and the seed layer 210 on the etched shape remain.

Figure 18:
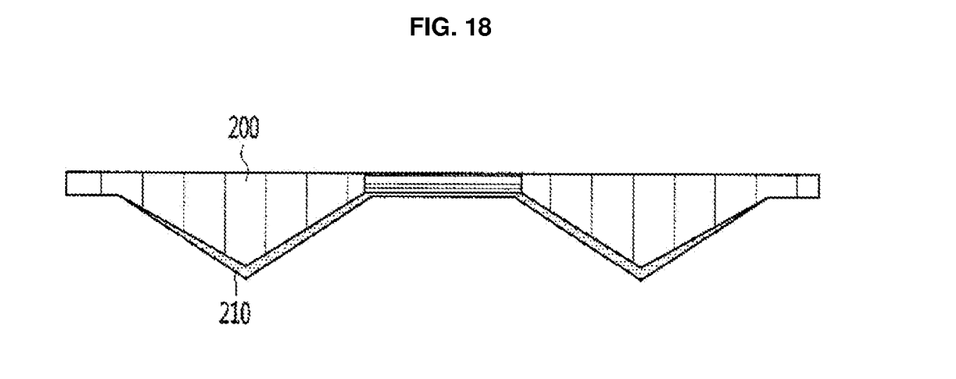

Referring to FIG. 18, a fifteenth step is to remove the substrate 105. The substrate 105 can be removed by wet etching, in which an etching solution containing KOH may be used. Accordingly, only the seed layer 210 on the etched shape and the metal layer 200 remain.

Figure 19:
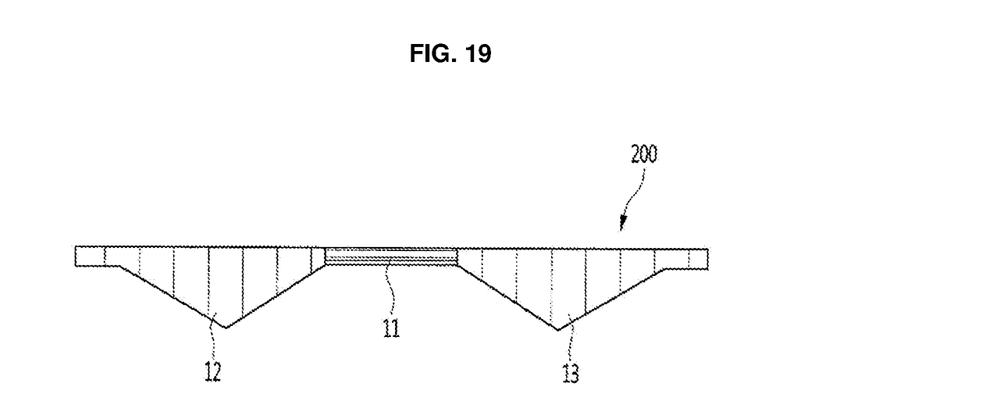

Referring to FIG. 19, a sixteenth step is to remove the seed layer 210 on the etched shape. Ammonia may be used to remove the seed layer 210. Accordingly, only the metal layer 200 remains, which corresponds to the ion generating device.

The metal layer 200, that is, the ion generating device includes the bed 11 and discharge pins 12 and 13. The angles θ of the discharge pins 12 and 13 may be 57.4°, and the width and height of the discharge pins may be 10 μm.

The discharge pins 12 and 13 are formed in a shape of which the width decreases downward from the bottom with a pointed tip. The bottoms of the discharge pins 12 and 13 depend on the shapes of the patterned portion 125 of the photosensitive resin layer 120 formed in the fourth step (see FIG. 7).

The shape of the patterned portion 125 of the photosensitive resin layer 120 depends on the shape of the opening 132 of the chrome layer 130 of the photo mask 130 and 140, and becomes the shapes of the bottoms of the discharge pins 12 and 13. The patterned portion 125 of the photosensitive resin layer 120 may be formed in a size of 10 μm or less such that the widths of the bottoms of the discharge pins 12 and 13 is 10 μm or less.

Accordingly, when the opening 132 of the chrome layer 130 of the photo mask 130 and 140 has a polygonal shape, the discharge pins 12 and 13 are formed in a pyramid shape. Further, when the opening 132 of the chrome layer 130 of the photo mask 130 and 140 has a circular shape, the discharge pins 13 and 14 are formed a conical shape. For example, when the opening 132 of the chrome layer 130 has a rectangular shape, the discharge pins 12 and 13 are formed in a square-based pyramid shape, and when the opening 132 of the chrome layer 130 has a circular shape, discharge pins 12 and 13 are formed in a conical shape.

The discharge pins 12 and 13 are made of nickel (Ni) and the bed 11 may also be made of nickel (Ni). However, the bed 11 may be made of metal that is not nickel. That is, the bed 11 has only to be a conductor.

The manufacturing process of the ion generating device may include a step of plating the discharge pins 12 and 13 with Platinum (Pt). Accordingly, a Platinum coating (Pt) is formed on the discharge pins 12 and 13, so the discharge efficiency can be further improved.

As described above, by minimizing a radius of a discharge pin by manufacturing a discharge electrode through a MEMS process, the intensity of voltage that is applied to the ion generating device can be reduced, so ozone and discharge noise that are generated by the ion generating device can be reduced.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method of manufacturing an ion generating device including a discharge electrode, the method comprising:
   forming a first pattern having an etched shape on a substrate;
   depositing a seed layer on the substrate with the first pattern;
   forming a metal layer on the seed layer, the forming of the metal layer on the seed layer including:
      coating a first photosensitive resin layer on the seed layer;
      putting a plurality of first photo masks on the first photosensitive resin layer and forming a second pattern on the first photosensitive resin layer by radiating first ultraviolet rays;
      exposing a portion of the seed layer as the first photosensitive resin layer forms the second pattern; and
      forming the metal layer on a top layer of the exposed portion of the seed layer;
   planarizing a top of the metal layer;
   removing the substrate; and
   removing the seed layer, wherein the substrate is made of silicon having crystal direction, wherein the etched shape of the substrate is formed by wet etching using potassium hydroxide, and wherein the metal layer formed by removing the substrate and the seed layer corresponds to the discharge electrode including a bed and a discharge pin.

2. The method of claim 1, wherein the forming the first pattern having the etched shape on the substrate includes:
   forming a sacrifice layer on the substrate;
   etching a portion of the sacrifice layer such that a portion of a top of the substrate is exposed; and
   forming the etched shape by wet-etching the exposed portion of the top of the substrate.

3. The method of claim 2, wherein the etching of the portion of the sacrifice layer includes:
   depositing a second photosensitive resin layer on the sacrifice layer and then exposing the second photosensitive resin layer to second ultraviolet rays through a second photo mask;
   exposing a portion of the sacrifice layer by forming a third pattern on the second photosensitive resin layer using a developing solution;
   exposing a portion of the substrate by forming a fourth pattern by etching the exposed portion of the sacrifice layer; and
   removing the second photosensitive resin layer.

4. The method of claim 3, wherein the second photo mask includes a glass plated with a chrome layer having a predetermined pattern, wherein the second photosensitive resin layer includes a photoresist that generates a chemical change when receiving light, wherein the second ultraviolet rays travel to the second photosensitive resin layer through an opening in the chrome layer, and wherein a first part of the second photosensitive resin layer not exposed to the second ultraviolet rays is not changed and a second part exposed to the second ultraviolet rays is cured.

5. The method of claim 4, wherein the developing solution melts the portion cured by the second ultraviolet rays of the second photosensitive resin layer to form the pattern on the second photosensitive resin layer.

6. The method of claim 2, wherein forming the sacrifice layer on the substrate includes:
   preparing and cleaning the substrate, and depositing the sacrifice layer on the substrate by Low Pressure Chemical Vapor Deposition.

7. The method of claim 2, wherein the etched shape of the substrate is formed with a narrower width towards an inside, and the etched shape corresponds to a shape of the discharge pin.

8. The method of claim 2, wherein the substrate and the seed layer are removed by wet etching, and wherein the sacrifice layer is removed by dry etching.

9. The method of claim 1, wherein the metal layer is formed by plating nickel.

10. The method of claim 1, further comprising forming a platinum coating on the metal layer.

11. A method of manufacturing an ion generating device including a discharge electrode, the method comprising:
   forming a first pattern having an etched shape on a substrate;
   depositing a seed layer on the substrate with the first pattern;
   forming a metal layer on the seed layer;
   planarizing a top of the metal layer;
   removing the substrate and the seed layer such that the metal layer formed by removing the substrate and the seed layer corresponds to the discharge electrode including a bed and a discharge pin; and removing the seed layer, wherein the forming of the first pattern having the etched shape on the substrate includes:

forming a sacrifice layer on the substrate;

etching a portion of the sacrifice layer such that a portion of a top of the substrate is exposed; and forming the etched shape by wet-etching the exposed portion of the top of the substrate using potassium hydroxide, wherein the etched shape of the substrate is formed with a narrower width towards an inside and corresponds to a shape of the discharge pin, wherein the forming the metal layer on the seed layer includes:

coating a first photosensitive resin layer on the seed layer;

putting a plurality of first photo masks on the first photosensitive resin layer and forming a second pattern on the first photosensitive resin layer by radiating ultraviolet rays;

exposing a portion of the seed layer as the first photosensitive resin layer forms the second pattern; and forming the metal layer on a top layer of the exposed portion of the seed layer.

12. The method of claim 11, wherein the etching of the portion of the sacrifice layer includes:

depositing a second photosensitive resin layer on the sacrifice layer and then exposing the second photosensitive resin layer to ultraviolet rays through a second photo mask;

exposing a portion of the sacrifice layer by forming a third pattern on the second photosensitive resin layer using a developing solution;

exposing a portion of the substrate by forming a fourth pattern by etching the exposed portion of the sacrifice layer; and removing the second photosensitive resin layer.

13. The method of claim 12, wherein the second photo mask includes a glass plated with a chrome layer having a predetermined pattern, wherein the second photosensitive resin layer includes a photoresist that generates a chemical change when receiving light, wherein ultraviolet rays travel to the second photosensitive resin layer through an opening in the chrome layer, and wherein a first part of the second photosensitive resin layer not exposed to the ultraviolet rays is not changed and a second part exposed to the ultraviolet rays is cured.

* * * * *